(12) United States Patent
Duck et al.

(10) Patent No.: US 10,359,139 B2
(45) Date of Patent: Jul. 23, 2019

(54) CONNECTOR

(75) Inventors: Benjamin S. Duck, Johnsburg, IL (US); John Henry Kutsch, Harvard, IL (US)

(73) Assignee: Medline Industries, Inc., Northfield, IL (US)

( * ) Notice: Subject to any disclaimer, the term of this patent is extended or adjusted under 35 U.S.C. 154(b) by 1344 days.

(21) Appl. No.: 13/440,296

(22) Filed: Apr. 5, 2012

(65) Prior Publication Data

US 2013/0264821 A1 Oct. 10, 2013

(51) Int. Cl.
*F16L 37/02* (2006.01)
*F16L 37/56* (2006.01)
*A61M 39/10* (2006.01)

(52) U.S. Cl.
CPC .............. *F16L 37/02* (2013.01); *F16L 37/56* (2013.01); *A61M 2039/1027* (2013.01); *A61M 2039/1088* (2013.01)

(58) Field of Classification Search
USPC ................... 285/12, 305, 121, 134.1, 125.1; D23/262; D24/129; 604/523, 533, 534, 604/535, 538
See application file for complete search history.

(56) References Cited

U.S. PATENT DOCUMENTS

| | | | |
|---|---|---|---|
| 3,640,552 A | 2/1972 | Demler et al. | |
| 3,834,388 A * | 9/1974 | Sauer | 604/119 |
| 4,557,261 A * | 12/1985 | Ru/ gheimer | 604/533 |
| 4,580,816 A | 4/1986 | Quitsch et al. | |
| 4,683,894 A | 8/1987 | Kodama et al. | |
| 4,779,625 A | 10/1988 | Cole | |
| 5,184,742 A | 2/1993 | DeCaprio et al. | |
| 5,273,254 A | 12/1993 | McNaughton et al. | |
| 5,413,582 A | 5/1995 | Eaton | |
| 5,511,552 A | 4/1996 | Johnson | |
| 6,095,983 A | 8/2000 | Wawro | |
| 6,344,025 B1 | 2/2002 | Inagaki et al. | |

(Continued)

FOREIGN PATENT DOCUMENTS

| | | |
|---|---|---|
| EP | 1355099 | 10/2003 |
| EP | 1380791 | 1/2004 |

(Continued)

OTHER PUBLICATIONS

Drager, "Publication", *Drager Blood Pressure Cuffs for Adult Patients*; pp. 1-4.

(Continued)

*Primary Examiner* — Aaron M Dunwoody
(74) *Attorney, Agent, or Firm* — Philip H. Burrus, IV

(57) ABSTRACT

A connector assembly (2100,3100) includes a unitary female connector portion (100) manufactured from a singular material that includes a waisted, tapering intermediate section (101) disposed between a compression ring (102) and a luminal connector (103) and one or more finger-grasping surfaces (108,109) disposed along the waisted, tapering intermediate section. A unitary male connector portion (1200,2200), which can be single ended or double-ended, includes a protruding male connector portion (1202,2202), one or more luminal connectors (1203,2203,2233) and a convex frustum (201,1201) disposed between the protruding male connector portion and the single ended luminal connector.

19 Claims, 14 Drawing Sheets

(56) References Cited

U.S. PATENT DOCUMENTS

| | | | |
|---|---|---|---|
| 6,578,428 | B1 | 6/2003 | Dromms et al. |
| D484,593 | S | 12/2003 | Baillargeon et al. |
| D485,616 | S | 1/2004 | Baillargeon et al. |
| D488,866 | S | 4/2004 | O'Dell |
| 6,796,186 | B2 | 9/2004 | Lia et al. |
| 7,121,592 | B2 | 10/2006 | Sazbo et al. |
| D557,414 | S | 12/2007 | Wentling |
| 7,670,296 | B2 | 3/2010 | Molnar et al. |
| 7,722,542 | B2 | 5/2010 | Lia et al. |
| 7,780,603 | B2 | 8/2010 | Lia |
| 7,811,278 | B2 | 10/2010 | Knipple et al. |
| D629,891 | S | 12/2010 | Virr et al. |
| D629,892 | S | 12/2010 | Hill et al. |
| D629,894 | S * | 12/2010 | Lombardi et al. ........... D24/129 |
| D642,244 | S | 7/2011 | Wilhelm |
| 7,976,071 | B2 | 7/2011 | Bibby |
| D649,240 | S | 11/2011 | Lewis et al. |
| D652,511 | S | 1/2012 | Lombardi et al. |
| D652,917 | S | 1/2012 | Hill et al. |
| D654,166 | S | 2/2012 | Lair |
| D698,440 | S | 1/2014 | Lombardi et al. |
| 8,696,037 | B2 | 4/2014 | Nakamura |
| 8,764,668 | B2 | 7/2014 | Roteliuk et al. |
| 9,061,130 | B2 | 6/2015 | Truitt |
| 9,089,682 | B2 | 7/2015 | Yeh et al. |
| D737,952 | S | 9/2015 | Matsumura |
| D741,477 | S | 10/2015 | Rogers |
| 2001/0005777 | A1 | 6/2001 | Nakagawa et al. |
| 2004/0181156 | A1 | 8/2004 | Kingsford et al. |
| 2006/0293600 | A1 | 12/2006 | Wawro et al. |
| 2007/0088327 | A1 | 4/2007 | Guala |
| 2008/0139950 | A1 | 6/2008 | Molnar et al. |
| 2008/0214993 | A1 * | 9/2008 | Haarala et al. ................. 604/44 |
| 2010/0056933 | A1 | 3/2010 | Grabl et al. |
| 2011/0012340 | A1 * | 1/2011 | Packham et al. ............... 285/84 |
| 2012/0016345 | A1 * | 1/2012 | Carter et al. .................. 604/533 |
| 2013/0264821 | A1 | 10/2013 | Duck |
| 2013/0320672 | A1 | 12/2013 | Steele |
| 2013/0338608 | A1 | 12/2013 | Moorehead et al. |
| 2014/0250664 | A1 | 9/2014 | Burgess et al. |
| 2015/0105737 | A1 | 4/2015 | Lopez et al. |

FOREIGN PATENT DOCUMENTS

| | | |
|---|---|---|
| EP | 1584348 | 10/2005 |
| EP | 1584348 B1 | 10/2005 |
| EP | 1770321 | 4/2007 |
| EP | 2158935 A1 | 3/2010 |
| WO | WO-2008/073428 | 6/2008 |

OTHER PUBLICATIONS

Mecury Medical, "Publication", *Mercury Medical POPPA BDR; Blood Pressure Connector, Cuffs, and Accessories*.

"Final Office Action Response", U.S. Appl. No. 11/513,608; Response Filed Jun. 30, 2010; Office Action dated Apr. 30, 2010.

Price, Ieisha "Restriction Requirement", U.S. Appl. No. 29/417,606, filed Apr. 5, 2012; dated Sep. 11, 2014.

Price, Ieisha "Ex Parte Quayle Action", U.S. Appl. No. 29/417,606, filed Apr. 5, 2012; dated Mar. 23, 2015.

"5-in-1 Suction Containers" [online] Unknown Publication date but believed to be prior to present application filing date [retrieved Sep. 2, 2015]; Retrieved from http://www.medline.com/catalog/catalog.jsp.

"6-in-1 Suction Containers" [online] Unknown Publication date but believed to be prior to present application filing date [retrieved Sep. 2, 2015]; Retrieved from http://www.medline.com/catalog/catalog.jsp.

"AirLife Omni-Flex Patient Connector by Carefusion"; [online] Unknown Publication date but believed to be prior to present application filing date [retrieved Sep. 2, 2015]; Retrieved from http://www.medline.com/catalog/catalog.jsp.

"AirLife Tubing Connectors by Carefusion"; [online] Unknown Publication date but believed to be prior to present application filing date [retrieved Sep. 2, 2015]; Retrieved from http://www.medline.com/catalog/catalog.jsp.

"Anesthesia Accessories and Connectors and by Smiths Medical"; [online] Unknown Publication date but believed to be prior to present application filing date [retrieved Sep. 2, 2015]; Retrieved from http://www.medline.com/catalog/catalog.jsp.

"Anesthesia Breathing Circuit Accessories by Smiths Medical"; [online] Unknown Publication date but believed to be prior to present application filing date [retrieved Sep. 2, 2015]; Retrieved from http://www.medline.com/catalog/catalog.jsp.

"Anesthesia Connector" [online] Unknown Publication date but believed to be prior to present application filing date [retrieved Sep. 2, 2015]; Retrieved from http://www.medline.com/catalog/catalog.jsp.

"Argyle Cpap Nasal Cannulas by Covidien" [online] Unknown Publication date but believed to be prior to present application filing date [retrieved Sep. 2, 2015]; Retrieved from http://www.medline.com/catalog/catalog.jsp.

"Argyle Tubing Connectors by Covidien" [online] Unknown Publication date but believed to be prior to present application filing date [retrieved Sep. 2, 2015]; Retrieved from http://www.medline.com/catalog/catalog.jsp.

"Blood Pressure Connector by Welch Allyn"; [online] Unknown Publication date but believed to be prior to present application filing date [retrieved Sep. 2, 2015]; Retrieved from http://www.medline.com/catalog/catalog.jsp.

"Concha Tubing Adapter by Teleflex" [online] Unknown Publication date but believed to be prior to present application filing date [retrieved Sep. 2, 2015]; Retrieved from http://www.medline.com/catalog/catalog.jsp.

"Five-in-One Tubing Connector by Covidien" [online] Unknown Publication date but believed to be prior to present application filing date [retrieved Sep. 2, 2015]; Retrieved from http://www.medline.com/catalog/catalog.jsp.

"Invacare Humidifier Connector" [online] Unknown Publication date but believed to be prior to present application filing date [retrieved Sep. 2, 2015]; Retrieved from http://www.medline.com/catalog/catalog.jsp.

"Latex-Free Coil Tubing with Connectors" [online] Unknown Publication date but believed to be prior to present application filing date [retrieved Sep. 2, 2015]; Retrieved from http://www.medline.com/catalog/catalog.jsp.

"Oxygen Adapters" [online] Unknown Publication date but believed to be prior to present application filing date [retrieved Sep. 2, 2015]; Retrieved from http://www.medline.com/catalog/catalog.jsp.

"Oxygen Supply Tubing by Teleflex" [online] Unknown Publication date but believed to be prior to present application filing date [retrieved Sep. 2, 2015]; Retrieved from http://www.medline.com/catalog/catalog.jsp.

"Oxygen Supply Tubing Connectors by Ti-Anim Health" [online] Unknown Publication date but believed to be prior to present application filing date [retrieved Sep. 2, 2015]; Retrieved from http://www.medline.com/catalog/catalog.jsp.

"Receptal Double Male Elbow Tubing Connectors by Hospira" [online] Unknown Publication date but believed to be prior to present application filing date [retrieved Sep. 2, 2015]; Retrieved from http://www.medline.com/catalog/catalog.jsp.

"Sterile Non-Conductive Suction Tubing;" [online] Unknown Publication date but believed to be prior to present application filing date [retrieved Sep. 2, 2015]; Retrieved from http://www.medline.com/catalog/catalog.jsp.

"Swivel Connectors by Salter Labs" [online] Unknown Publication date but believed to be prior to present application filing date [retrieved Sep. 2, 2015]; Retrieved from http://www.medline.com/catalog/catalog.jsp.

"Tubing Adapters by DeRoyal" [online] Unknown Publication date but believed to be prior to present application filing date [retrieved Sep. 2, 2015]; Retrieved from http://www.medline.com/catalog/catalog.jsp.

(56) References Cited

OTHER PUBLICATIONS

"Tubing Connector by Welch Allyn" [online] Unknown Publication date but believed to be prior to present application filing date [retrieved Sep. 2, 2015]; Retrieved from http://www.medline.com/catalog/catalog.jsp.

"Tubing Connectors by Cardinal Health" [online] Unknown Publication date but believed to be prior to present application filing date [retrieved Sep. 2, 2015]; Retrieved from http://www.medline.com/catalog/catalog.jsp.

"Tubing Connectors by Salter Labs" [online] Unknown Publication date but believed to be prior to present application filing date [retrieved Sep. 2, 2015]; Retrieved from http://www.medline.com/catalog/catalog.jsp.

Price, Iesha, "Notice of Allowance", U.S. Appl. No. 29/417,606; Filed Apr. 5, 2012; dated Apr. 21, 2016.

\* cited by examiner

US 10,359,139 B2

CONNECTOR

BACKGROUND

Technical Field

This invention relates generally to a connector, and more particularly to a connector configured for use in selective coupling of flexible hose or tubing.

Background Art

Plug-type connectors are used to connect hoses or tubing in vacuum, acoustic, and fluid conduit applications. When using such a connector, a flexible hose or tube is passed over a male connector having ramped protrusions angled along the insertion direction. To retain the hose or tube on the connector, the ramped barb portions are configured to mechanically engage the hose or tubing if the same is pulled in a direction away from the connector. Such connectors can be used to couple a tube coming from one device or instrument to a tube coming from another device. For example, a vacuum or air pump having a hose extending therefrom can be coupled to a bladder or balloon having a tube extending therefrom by using a connector to connect the hose to the tube.

These prior art connectors become problematic when a user needs to remove the hose or tubing from the connector. Using the vacuum or air pump example from above, when the user wants to separate the devices by removing the hose from the tube, the ramped barb portions can damage the hose, tubing, or both. Further, depending upon the mechanical configuration of the ramped barb portions, their shape can make removal of the hose or tube prohibitively difficult.

There is accordingly a need for a new connector.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the present invention.

Figure 1:
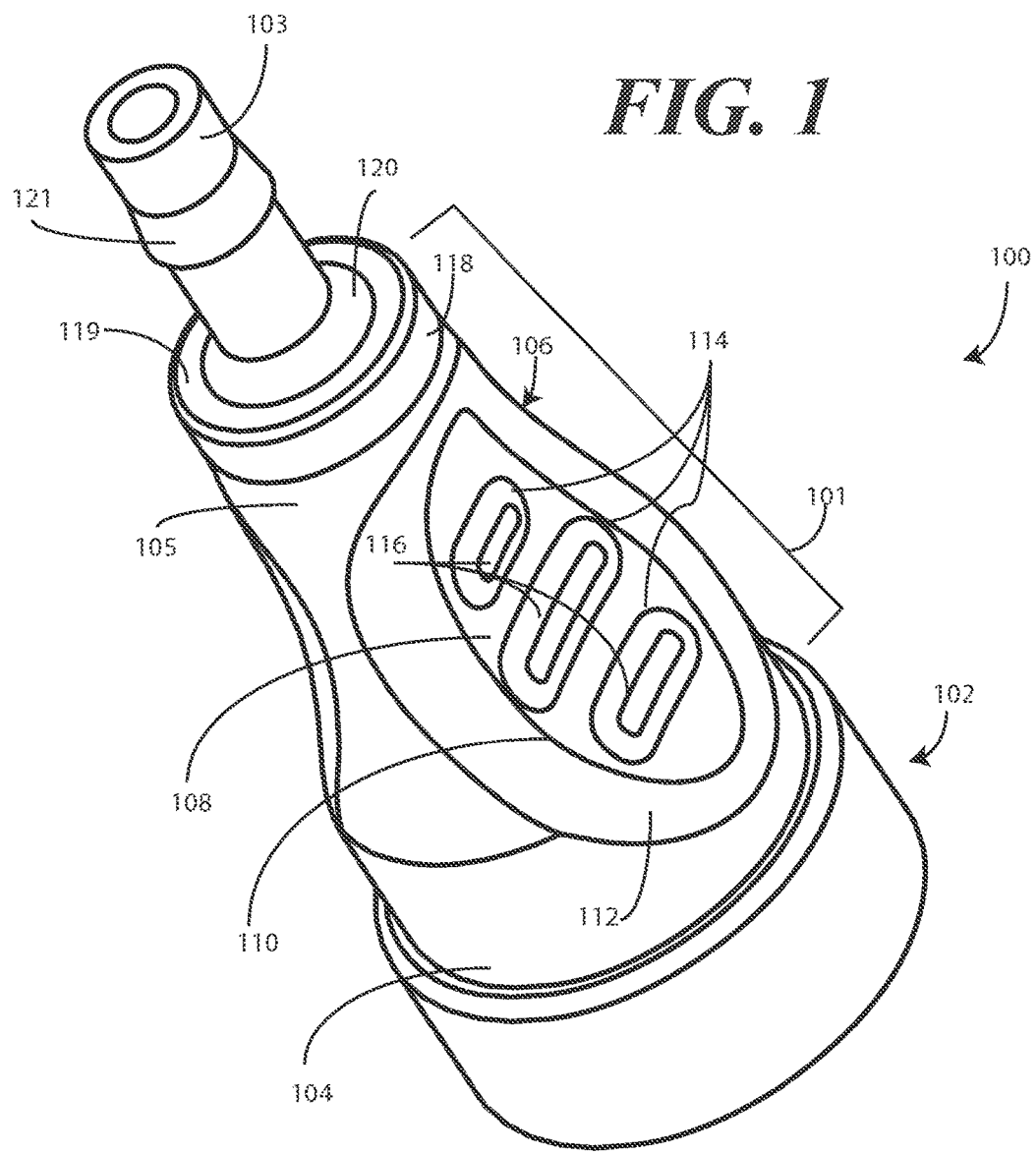
FIG. 1 illustrates a perspective view of one unitary single ended female connector portion configured in accordance with one or more embodiments of the invention.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION OF EMBODIMENTS OF THE INVENTION

Embodiments of the invention are now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on." Relational terms such as first and second, top and bottom, and the like may be used solely to distinguish one entity or action from another entity or action without necessarily requiring or implying any actual such relationship or order between such entities or actions. Also, reference designators shown herein in parenthesis indicate components shown in a figure other than the one in discussion. For example, talking about a device (10) while discussing figure A would refer to an element, 10, shown in figure other than figure A. Further, it is expected that one of ordinary skill, notwithstanding possibly significant effort and many design choices motivated by, for example, available time, current technology, and economic considerations, when guided by the concepts and principles disclosed herein will be readily capable of generating such connector portions with minimal experimentation.

Embodiments of the present invention provide a connector assembly suitable for coupling sections of flexible conduit, such as tubing or hose, together. Portions of the connector assembly can be separated, thereby allowing coupled tubing or hose to be separated without barb fittings damaging the same. For example, in one embodiment a female connector portion and either a single ended male connector portion or a double-ended male connector portion to selectively be coupled together or taken apart as needed in a particular environment. The detachability of the female and male connector portions prevents wear and tear on the conduit coupled to each portion.

In one explanatory application, the connector is suitable for use in a blood pressure cuff application. While it will be clear to those of ordinary skill in the art having the benefit of this disclosure that the connector is well suited for any number of applications where flexible hoses or tubing needs to be coupled together, a blood pressure cuff application will be used herein as an explanatory example for ease of illustration. Blood pressure applications are well suited for connector assemblies described below because disposable blood pressure cuffs are frequently used in hospitals and medical facilities and require various flexible tubes coupled to machines and cuffs to be attached or detached from each other. In such an application, for instance, the female connector portion can be coupled to a flexible tube extending from a blood pressure cuff, while either the single ended male connector portion or the double-ended male connector portion is coupled to another flexible tube or tubes extending from the transducer of the sphygmomanometer. Where the sphygmomanometer is configured to both inflate the cuff and measure blood pressure from a single flexible tube, the single ended male connector portion can be used. Where the sphygmomanometer is configured to inflate the cuff with a first tube and measure pressure with another, the double-ended male connector portion can be used.

A luminal connector of the female connector portion can first be coupled to the tube coupled to the blood pressure cuff. One or more luminal connectors of the male connector portion can be coupled to the tube(s) coupled to the sphygmomanometer. When blood pressure is taken, rather than tediously manipulating the tubing, the male and female connector portions can quickly be coupled together or taken apart without the need for alignment features or special techniques.

The use of the connector assemblies of the present invention offers numerous advantages over prior art connectors. For example, embodiments described herein are unitary in that they are manufactured solely from a single type of material. This single material can be molded in a single tube, thereby saving cost. There is no need for insert molding to incorporate components manufactured from disparate materials together. Nor is there a need to glue, solder, or otherwise couple components such as O-rings to connector housings. While prior art connectors can include metal and O-rings in combination, or plastic and rubberized O-rings in combination, embodiments of the present invention provide connector portions formed as a single piece of molded material. This can result in a cost savings as well. Some prior art connectors can cost as much as twelve dollars to manufacture, while embodiments of the present invention can be manufactured for as little as thirty cents.

Second, embodiments of the present invention are easy to assemble. In one embodiment, a female connector portion is manufactured from a pliable elastomeric thermoplastic, such as Santoprene™, while a male connector portion is manufactured from a rigid material such as polypropylene. The male connector portion can include a protruding male connector configured with radial snap fitting recesses, while the female connector portion includes an insertion region having radial snap fitting protrusions surrounded by an annular compression ring. (Note that the radial snap fitting recesses can be on the female connector portion while the radial snap fitting protrusions are on the male connector portion as well). The two connector portions can be easily connected by inserting the protruding male connector into the insertion region such that the radial snap fitting protrusions mate with the radial snap fitting recesses. In one embodiment, the radial snap fitting protrusions and radial snap fitting recesses are configured to produce a "snap" sound that serves as an audible signal that the two parts have been properly coupled together and/or that an air-tight or liquid-tight seal has been formed therebetween. (Note that the airtight or liquid-tight seal can be formed without O-rings due to the uniqueness of design described in the present application.) The two connector portions can be separated by pulling the two portions apart. The depth of the radial snap fitting protrusions and radial snap fitting recesses can be specifically designed so that the portions will not be pulled apart during normal use.

Another advantage of embodiments of the present invention over prior art designs is the minimization of the risk of skin irritation occurring due to the connector. This advantage is highlighted in the blood pressure application. In many hospitals, for instance, tubing and hoses may be coupled together with at least one tube or hose coupled to a patient while another is coupled to a machine. Blood pressure machines can be coupled to cuffs continually placed about a patient's arm to take blood pressure readings at periodic intervals. In such an application, the patient may tend to roll or otherwise cover the connector. The single material construction using, for instance, Santoprene™ that covers portions of a polypropylene material, the risk for skin irritation is greatly reduced. Moreover, the smoothly contoured design of embodiments described herein eliminates hard corners to further increase patient comfort should the patient find himself or herself atop the connector.

Another advantage of embodiments of the present invention is that no metal components are required. Accordingly, there is no concern about the connector interfering with the operation of machines and devices located in health care environments, such as magnetic resonance imaging machines and the like.

Another advantage of embodiments of the present invention is that the male connector portions and female connector portions of the present invention provide a universal connector solution that is not dependent upon a particular tubing size or device configuration. Prior art designs frequently use expensive Y-type connectors to couple, for example, blood pressure monitoring equipment and a blood pressure cuff, which may be disposable. There are a multitude of such connectors, each being specifically designed for a particular type of equipment. There is a risk that use of the improper Y-connector can result in misalignment or improper coupling when a cuff and monitoring device employ disparate tubing configurations. With embodiments of the present invention, one universal female connector portion can be manufactured with a variety of luminal connector configurations (as can the male connector portion) so that a female connector portion having a first type of luminal connector can be coupled to a male connector having a second type of luminal connector. This, of course, is not possible with a Y-type connector where each tubing connection is fixed. The universal feature of embodiments of the present invention reduces the risk of cross contamination and tubing misconnections.

Yet another advantage of embodiments of the invention is that the female connector portions and male connector portions are easily coupled together due to a straight-line axis of insertion. This, along with the fact that no clasping mechanisms are required due to the unique design of the compression ring of the female connector portion, allows a user to couple and/or decouple the connector portions from each other with a single hand.

Yet another advantage of embodiments of the present invention is that the connector portions can rotate 360 degrees about the straight-line axis of insertion without affecting the coupling between the connector portions. This is a distinct advantage when compared to asymmetrical connectors, such as Y-type connectors, in that there need not be any specific alignment between the connector portions prior to coupling the same together.

The use of rigid thermoplastics for the male portion and elastomeric thermoplastics for the female portion also provides the advantage of allowing printing of text, graphics, and other indicia along either the female connector portion or the male connector portion. For example, in one embodiment, the words "do not discard" can be molded, etched, or otherwise disposed along the male connector portion or female connector portion to help prevent the connector from being thrown away. In one blood pressure embodiment, the male connector portion is coupled to a blood pressure monitoring machine while the female connector portion is coupled to a disposable blood pressure cuff. Accordingly, molding "do not discard" into the male connector solves the problem of the equipment-side connectors being thrown away.

Yet another advantage of providing a two-piece female connector portion-male connector portion assembly is that the components can be sold separately. For example, in one embodiment, the female connector portion can be integrated into a disposable blood pressure cuff assembly. This combination can be sold as a single unit from the manufacturer. Similarly, the male connector can be sold to a hospital or health care service provider for use with blood pressure monitoring equipment. Accordingly, the health care service provider needs only buy a portion of the connector assembly, thereby reducing overall cost, inventory requirements, and so forth.

Figure 4:
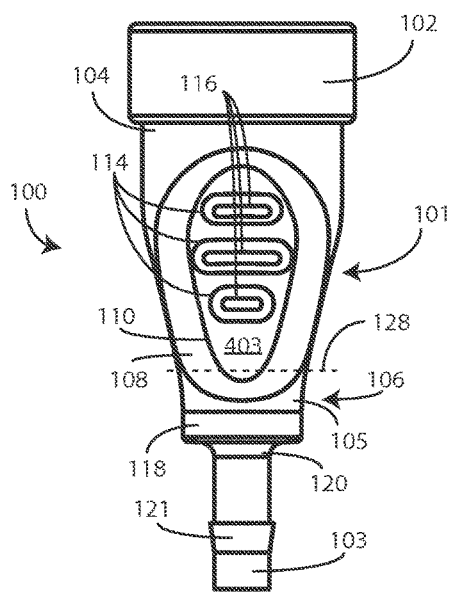
FIG. 4 illustrates a third side elevation view of one unitary single ended female connector portion configured in accordance with one or more embodiments of the invention.
Figure 5:
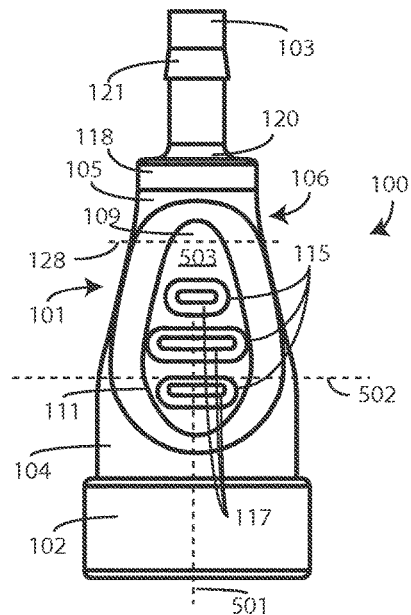
FIG. 5 illustrates a fourth side elevation view of one unitary single ended female connector portion configured in accordance with one or more embodiments of the invention.
Figure 6:
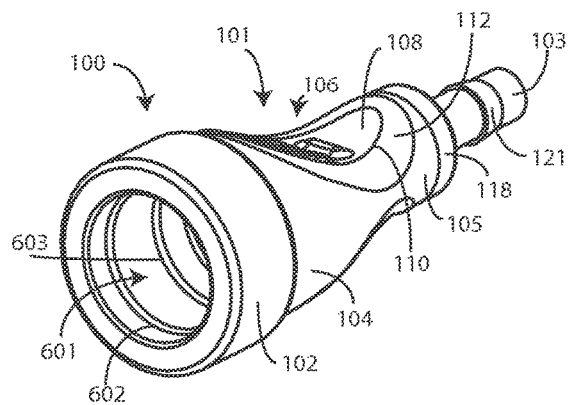
FIG. 6 illustrates a second perspective view of one unitary single ended female connector portion configured in accordance with one or more embodiments of the invention.
Figure 7:
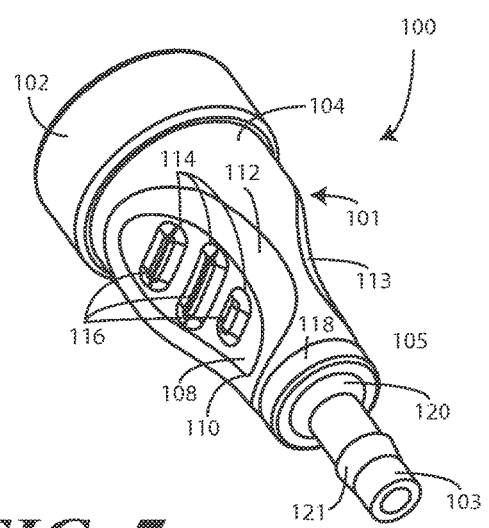
FIG. 7 illustrates a third perspective view of one unitary single ended female connector portion configured in accordance with one or more embodiments of the invention.
Figure 8:
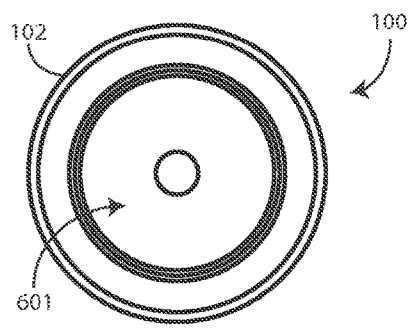
FIG. 8 illustrates a bottom plan view of one unitary single ended female connector portion configured in accordance with one or more embodiments of the invention.
Figure 9:
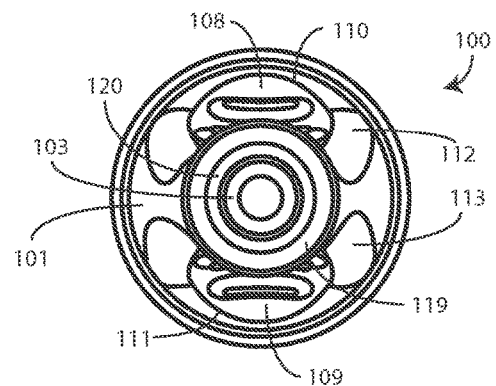
FIG. 9 illustrates a top plan view of one unitary single ended female connector portion configured in accordance with one or more embodiments of the invention.
Figure 10:
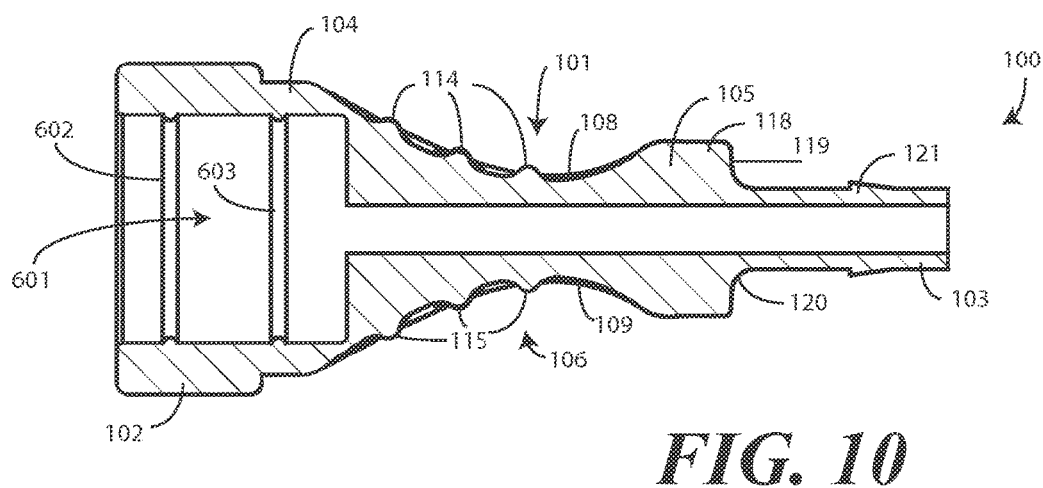
FIG. 10 illustrates a sectional view of one unitary single ended female connector portion configured in accordance with one or more embodiments of the invention.
Figure 11:
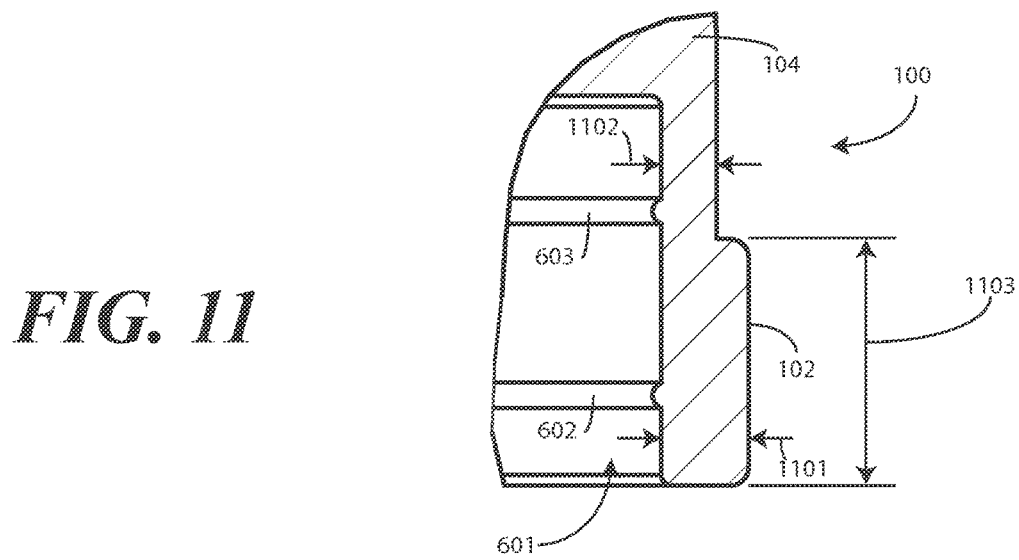
FIG. 11 illustrates a cut-away view of a compression ring of one unitary single ended female connector portion configured in accordance with one or more embodiments of the invention.

Turning now to FIGS. 1-11, illustrated therein is one embodiment of a unitary female connector portion 100 configured in accordance with one or more embodiments of the invention. FIGS. 1, 6, and 7 illustrate various perspective views, while FIGS. 2-5 illustrate side elevation views at 90-degree rotations. FIGS. 8 and 9 illustrate bottom and top plan views, respectively, while FIGS. 10 and 11 illustrate sectional views showing internal elements of the unitary female connector portion 100.

The unitary female connector portion 100 includes a waisted, tapering intermediate section 101 that is disposed between a compression ring 102 and a luminal connector 103. In one embodiment, the waisted, tapering intermediate section 101 has a length of about 1.08 inches. One or more finger-grasping surfaces 108,109 are disposed along the waisted, tapering intermediate section 101. In the illustrative embodiment of FIGS. 1-11, two finger-grasping surfaces 108,109 are shown disposed on opposite sides of the waisted, tapering intermediate section 101. A first finger-grasping surface 108 is disposed along the waisted, tapering intermediate section 101, with the second finger-grasping surface 109 disposed along the waisted, tapering intermediate section rotated 180 degrees relative to the first finger grasping surface. It will be clear to those of ordinary skill in the art having the benefit of this disclosure that three, four, or more finger grasping surfaces can be applied to the waisted, tapering intermediate section 101 as well. Where the finger grasping surfaces are disposed at periodic rotation intervals about the waisted, tapering intermediate section 101, three finger grasping surfaces could be disposed at 120-degree rotation intervals, four at 90-degree rotation intervals, and so forth. Non-periodic rotation intervals can be used as well.

The waisted, tapering intermediate section 101 is referred to as "tapering" because the overall thickness of the waisted, tapering intermediate section 101 diminishes or becomes reduced as the waisted, tapering intermediate section 101 passes from a base end 104 to a distal end 105. The waisted, tapering intermediate section 101 is referred two as "waisted" because a waist 106 or most narrow part is defined between the base end 104 and the distal end 105. In the illustrative embodiment of FIGS. 1-11, the waist 106 is a dual waist it includes two waist diameters, with a first waist diameter defined along a first axis being less than a second waist axis that is defined along a second axis that is substantially orthogonal with the first axis.

Figure 2:
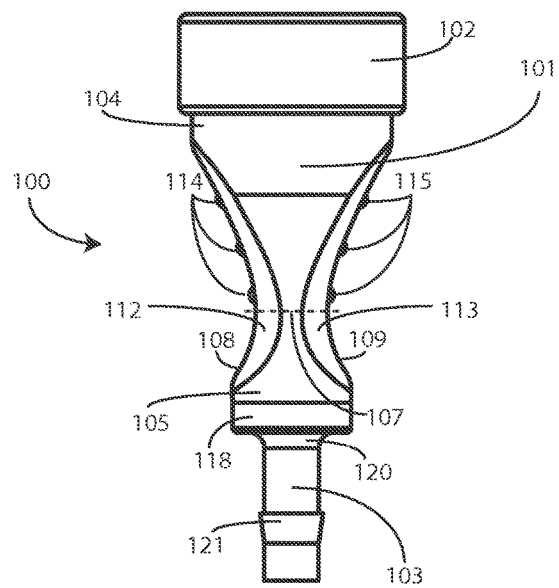
FIG. 2 illustrates a first side elevation view of one unitary single ended female connector portion configured in accordance with one or more embodiments of the invention.
Figure 3:
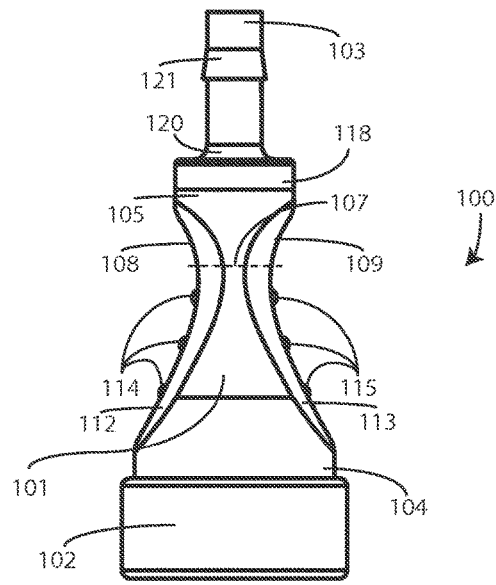
FIG. 3 illustrates a second side elevation view of one unitary single ended female connector portion configured in accordance with one or more embodiments of the invention.

For example, as shown in FIGS. 2 and 3, a first axis 107 is defined as by a line running between finger-grasping surfaces 108,109 at a location where the distance between the two finger-grasping surfaces 108,109 is at a minimum. The length of this minimum distance defines the first waist.

As shown in FIGS. 4 and 5, a second axis 128 is defined across the waisted, tapering intermediate section 101 at a rotational orientation that is substantially orthogonal relative to the first axis 107. Further, the second axis 128 occurs where the thickness of the waisted, tapering intermediate section 101 is a minimum. This thickness defines the second waist. In the illustrative embodiment of FIGS. 1-11, the second waist is greater than the first waist. This is most easily seen by comparing FIGS. 2 and 4, wherein the thickness of the waisted, tapering intermediate section 101 at axis 107 is less than the thickness of the waisted, tapering intermediate section 101 at axis 128. In other embodiments, the second waist can be less than the first waist, as will be clear to those of ordinary skill in the art having the benefit of this disclosure.

In the illustrative embodiment of FIGS. 1-11, the finger-grasping surfaces 108,109 are configured as scalloped finger grips. The finger-grasping surfaces 108,109 are referred to as "scalloped" because they are configured as convex rounded surfaces forming not only a comfortable and intuitive location to place one's fingers, but also as an ornamental edging formed into the waisted, tapering intermediate section 101. As shown best in FIGS. 4 and 5, in one embodiment the finger-grasping surfaces 108,109 comprise perimeters 110, 111 that are a semi-asymmetrically ovular. The perimeters 110,111 are semi-asymmetrically ovular because they are generally ovular and are symmetrical along a first axis 501 (shown in FIG. 5), but are not symmetrical along a second axis 502 (also shown in FIG. 5) that is orthogonal with the first axis 501. This semi-asymmetrically ovular perimeter 110,111 provides an aesthetically pleasing appearance that corresponds to the shape and contour of the waisted, tapering intermediate section 101. While this is one shape for the perimeters 110,111 of the finger-grasping surfaces 108,109, it will be clear to those of ordinary skill in the art having the benefit of this disclosure that other perimeters, such as rectangular perimeters, triangular perimeters, trapezoidal perimeters, and the like, can be used as well.

In the illustrative embodiment of FIGS. 1-11, each finger-grasping surface 108,109 is bounded by a transition surface 112,113. Since the finger-grasping surfaces 108,109 of this illustrative embodiment are semi-asymmetrically ovular, the transition surfaces 112,113 are also configured to be semi-asymmetrically ovular. The transition surfaces 112,113 are known as "transition" surfaces because their surfaces—or tangent lines of their surfaces—are non-planar with either the semi-asymmetrically ovular grasping planes 403,503 of the finger-grasping surfaces 108,109 or the surfaces—or tangent lines to the surfaces—of the remaining portions of the waisted, tapering intermediate section 101.

Each finger-grasping surface 108,109 of the illustrative embodiment includes a plurality of scalloped finger grips. For example, finger-grasping surface 108 has three scalloped finger grips 114. Similarly, finger-grasping surface 109 has three scalloped finger grips 115. Either finger-grasping surface 108,109 could have more or less finger grips, such as two, four, or more. In the illustrative embodiment, each scalloped finger grip 114,115 terminates at a planar finger grip segmentum 116,117. The planar finger grip segmenta 116,117 serve as a flat surfaces disposed along an otherwise convex scalloped finger grips 114,115 that aid in gripping the unitary female connector portion 100 in addition to providing an attractive textural appearance. While the planar finger grip segmenta 116,117 correspond in shape to the scalloped finger grips 114,115, i.e., each is oval when viewed in plan view, they could be differently shaped as well. A planar finger grip segmentum 116 could be rectangular, for example, while its corresponding scalloped finger grip 114 can be rounded.

The distal end 105 of the waisted, tapering intermediate section 101 of the illustrative embodiment terminates at a cylindrical intermediate section termination 118. Note that in other embodiments, the waisted, tapering intermediate section 101 could simply continue to taper until the luminal connector base 119 is reached. However, to provide both mechanical support and an aesthetically pleasing design, the illustrative unitary female connector portion 100 employs the cylindrical intermediate section termination 118.

The luminal connector base 119 in this embodiment is configured as a disk-shaped plane. The luminal connector base 119 extends from the cylindrical intermediate section termination 118 to a sloped luminal connector transition 120. The sloped luminal connector transition 120, which can be flat, convex, or concave, is configured in this embodiment as a convex surface running from the luminal connector base 119 to the bottom of the luminal connector 103.

The luminal connector 103 can include one or more barb fittings. In the illustrative embodiment, the luminal connector 103 includes a single barb fitting 121, which is configured as a ramp disposed along the luminal connector 103 about 0.13 inches from the end of the luminal connector and extending away from the luminal connector 103 as it moves toward the bottom of the luminal connector 103. In one embodiment the ramp has a length of about a tenth of an inch and terminates at a surface that is substantially orthogonal with the luminal connector 103. This barb fitting 121 allows a flexible hose or tubing to be passed over the top of the luminal connector 103 and passed over the barb fitting 121 to the sloped luminal connector transition 120. The surface substantially orthogonal with the luminal connector 103 is then able to grasp the flexible tubing and retain it along the luminal connector 103.

Disposed opposite the waisted, tapering intermediate section 101 is a compression ring 102. The compression ring and in some embodiments, the base end 104 of the waisted, tapering intermediate section 101, define an insertion region 601 of the unitary female connector portion 100. In one embodiment, the insertion region 601 is about 0.529 inches deep. The insertion region 601 defines a receiving chamber for a corresponding male connector portion to be inserted into the base of the unitary female connector portion 100.

The compression ring 102 in one embodiment has a thickness 1101 that is greater than the thickness 1102 of the walls of the waisted, tapering intermediate section 101. For example, in an illustrative embodiment, the thickness 1101 of the compression ring 102 is about 0.12 inches. In one embodiment, the compression ring has a length 1103 of about 0.33 inches. Experimental analysis has shown that these dimensions, which may vary within normal manufacturing tolerances, work well to retain the unitary female connector portion 100 to a corresponding male connector portion with a sufficiently airtight seal and suitable release forces for a blood pressure application. The perimeter of the interior wall of the compression ring 102, in one embodiment, is between about 0.499 inches and 0.524 inches.

The walls of the insertion region 601 can be configured with mechanical coupling features. In the illustrative embodiment, a plurality of radial snap fitting protrusions 602,603. Each of the explanatory snap fitting protrusions 602,603 has a height of about 0.12 inches. As will be seen in the subsequent figures, the radial snap fitting protrusions 602,603 can be configured to mate with radial snap fitting recesses on a complementary male connector portion. While radial snap fitting protrusions 602,603 are used in the unitary female connector portion 100, the complementary fitting element could be used instead. Said differently, the unitary female connector portion 100 could include radial snap fitting recesses, while the male connector portion could include the radial fitting protrusions. Alternatively, instead of recesses and protrusions, other mechanical coupling elements such as reversible barb fittings, ramp and latch fittings, friction fittings, and so forth could be used.

In one embodiment, the unitary female connector portion 100 is manufactured by a single material by way of an injection molding process where the entire part is made within a single tool. For instance, the unitary female connector portion 100 can be manufactured with an elastomeric thermoplastic material such as a silicone or other material. One suitable material is Santoprene™. The Santoprene™ or other elastomeric thermoplastic can be colored in some embodiments. In one embodiment, the elastomeric thermoplastic can be colored grey, with an explanatory example being PMS 430 grey.

Now that one example of the unitary female connector portion 100 has been described, attention will be paid to the male connector portion. As will be shown in the figures below, the male connector portion can come in different embodiments. For ease of illustration, two embodiments will be shown. The first is a single ended male connector portion and the second is a double-ended male connector portion. Two points of note: First, the two embodiments of the male connector portion are not the only embodiments contemplated within the scope of the present invention. Triple-ended connector portions or other types of connector portions will be obvious to those of ordinary skill in the art having the benefit of this disclosure. Second, the unitary female connector portion 100 could equally be configured as a double-ended connector portion, triple ended connector portion, and so forth.

Figure 12:
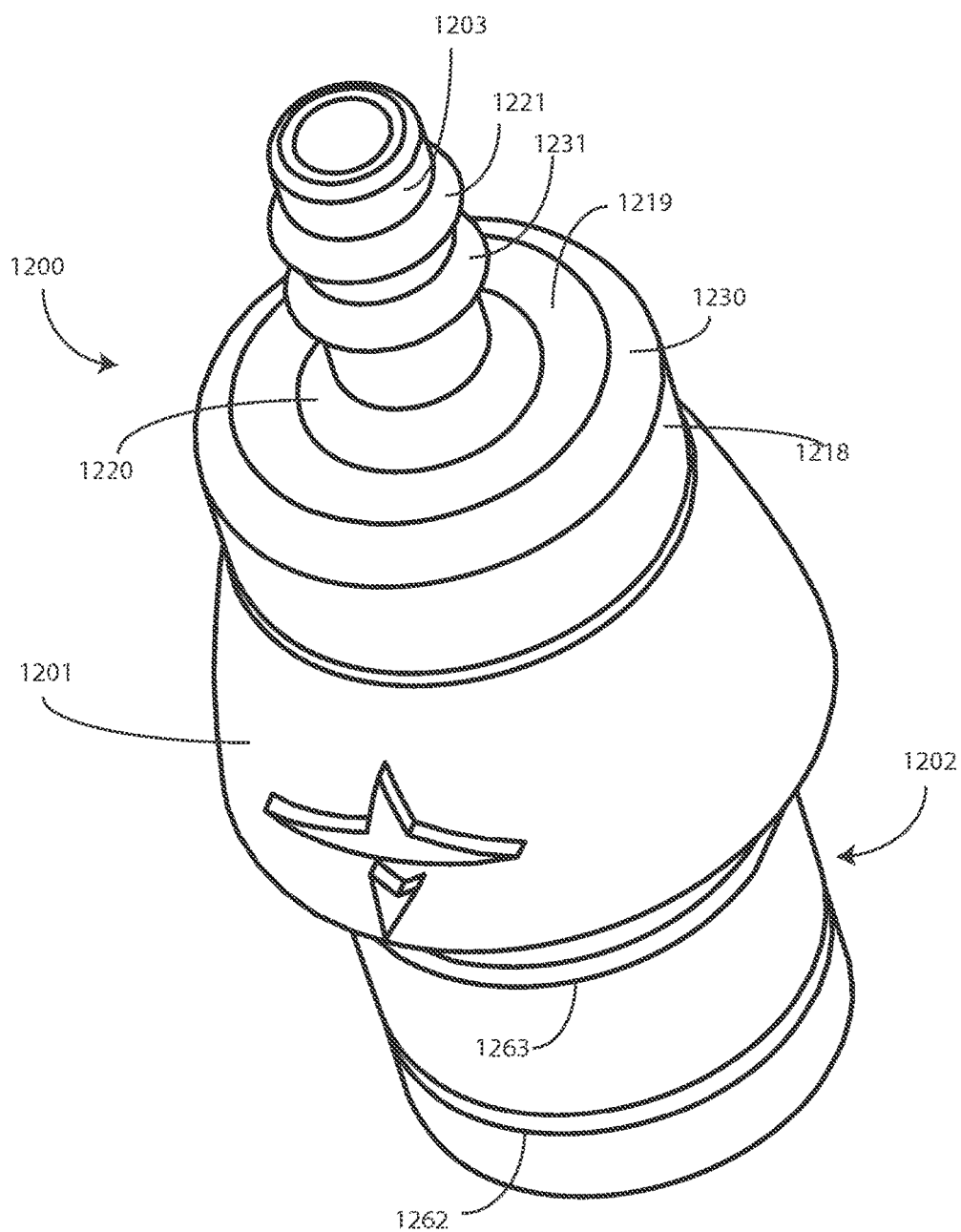
FIG. 12 illustrates a perspective view of one unitary single ended male connector portion configured in accordance with one or more embodiments of the invention.
Figure 13:
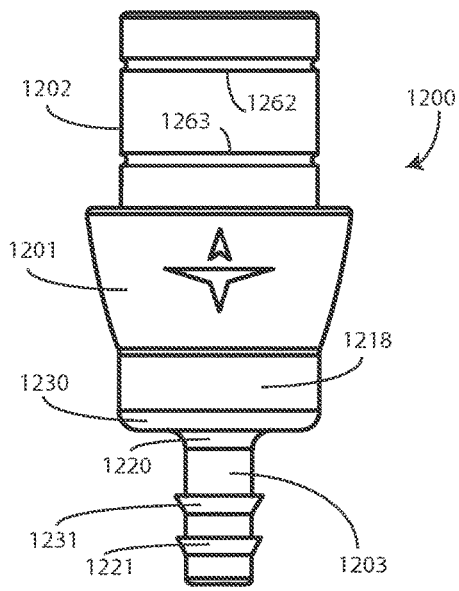
FIG. 13 illustrates a first side elevation view of one unitary single ended male connector portion configured in accordance with one or more embodiments of the invention.
Figure 14:
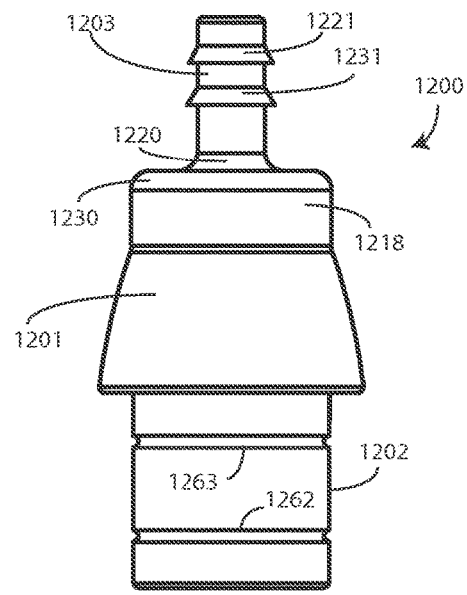
FIG. 14 illustrates a second side elevation view of one unitary single ended male connector portion configured in accordance with one or more embodiments of the invention.
Figure 15:
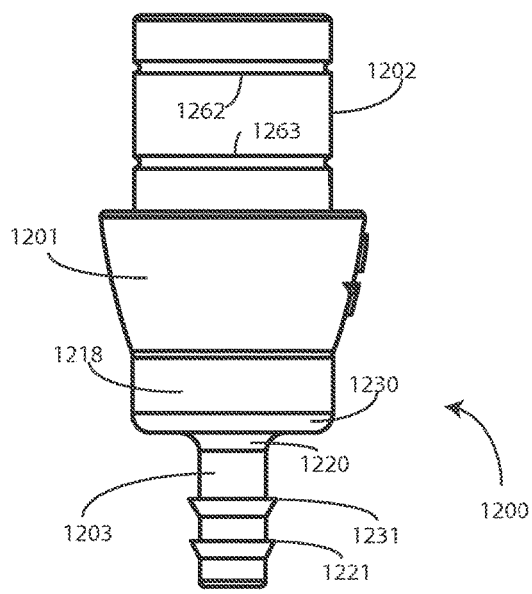
FIG. 15 illustrates a third side elevation view of one unitary single ended male connector portion configured in accordance with one or more embodiments of the invention.
Figure 16:
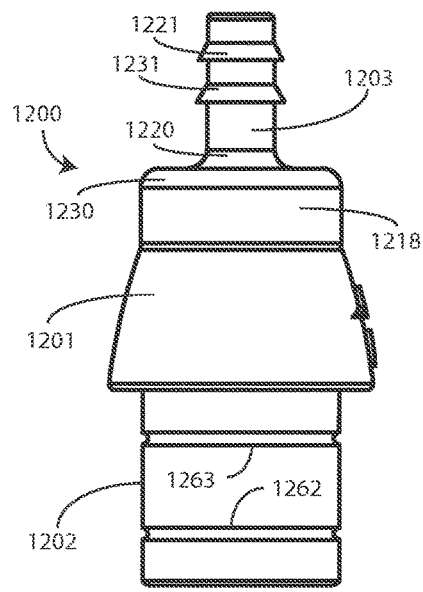
FIG. 16 illustrates a fourth side elevation view of one unitary single ended male connector portion configured in accordance with one or more embodiments of the invention.
Figure 17:
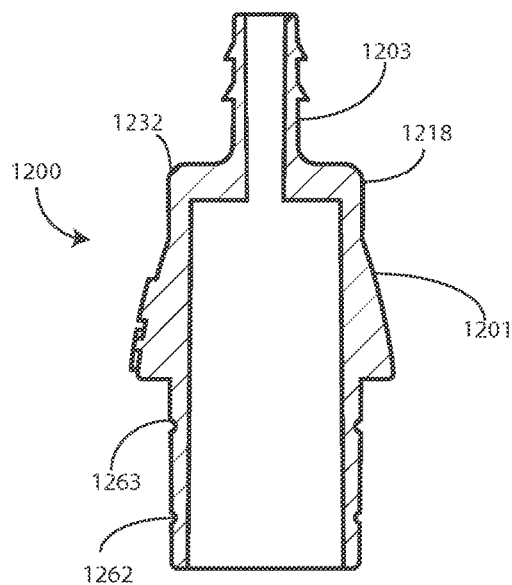
FIG. 17 illustrates a sectional view of one unitary single ended male connector portion configured in accordance with one or more embodiments of the invention.
Figure 18:
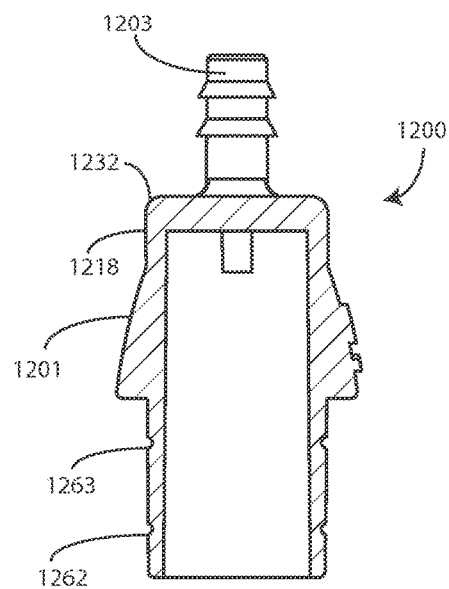
FIG. 18 illustrates a second sectional view of one unitary single ended male connector portion configured in accordance with one or more embodiments of the invention.
Figure 19:
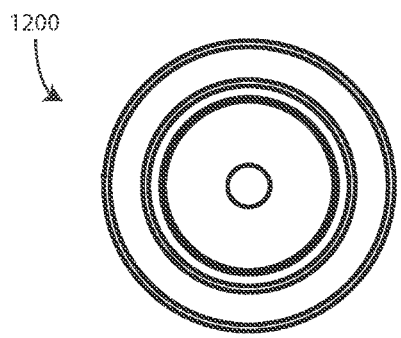
FIG. 19 illustrates a bottom plan view of one unitary single ended male connector portion configured in accordance with one or more embodiments of the invention.
Figure 20:
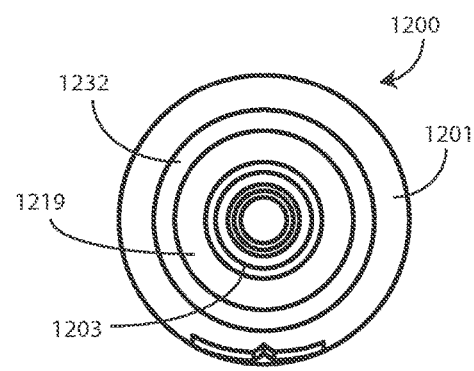
FIG. 20 illustrates a top plan view of one unitary single ended male connector portion configured in accordance with one or more embodiments of the invention.

Turning now to FIGS. 12-20, illustrated therein is one embodiment of a unitary male connector portion 1200 configured in accordance with one or more embodiments of the invention. The unitary male connector portion 1200 of FIGS. 12-20 is referred to as a "single ended" male connector portion because it includes a single luminal connector 1203. As will be shown below, FIGS. 22-30 show a unitary double-ended male connector portion (2200) having two luminal connectors (2203,2233). FIG. 12 illustrates a perspective view, while FIGS. 13-16 illustrate side elevation views at 90-degree rotations. FIGS. 19 and 20 illustrate bottom and top plan views, respectively, while FIGS. 17 and 18 illustrate sectional views showing internal elements of the unitary male connector portion 1200.

Many elements of the unitary male connector portion 1200 are similar to corresponding elements described above for the unitary female connector portion (100). For example, the unitary male connector portion includes a cylindrical segmentum 1218, which is similar to the cylindrical intermediate section termination (118) described above. While the end of the unitary male connector portion 1200 could simply continue to taper to its luminal connector base 1219, to provide both mechanical support and an aesthetically pleasing design, the illustrative unitary male connector portion 1200 employs a cylindrical segmentum 1218.

An annular transition surface 1232 is disposed between the cylindrical segmentum 1218 and the luminal connector base 1219. The annular transition surface 1232 of this illustrative embodiment is a convex surface having a circumference that narrows as the annular transition surface 1232 extends away from the cylindrical segmentum 1218. This provides a rounded contour that adds to the comfort of the overall connector portion when a patient inadvertently rolls over or otherwise finds himself or herself atop the unitary male connector portion 1200.

A second similarity between the unitary male connector portion 1200 and the unitary female connector portion (100) described above is the use of a luminal connector base 1219 configured as a disk-shaped plane. The luminal connector base 1219 extends from a rounded contour 1230 disposed between the cylindrical segmentum 1218 to the sloped luminal connector transition 1220. The sloped luminal connector transition 1220, which can be flat, convex, or concave, is configured in this embodiment as a convex surface running from the luminal connector base 1219 to the bottom of the luminal connector 1203.

The luminal connector 1203 can include one or more barb fittings. In the illustrative embodiment, the luminal connector 1203 includes two barb fittings 1221,1331, each which is configured as a ramp disposed along the luminal connector 1203. The first barb fitting 1221 begins near the end of the luminal connector 1203 and extending away from the luminal connector 1203 as it moves toward the bottom of the luminal connector 1203. The ramp terminates at a surface that is substantially orthogonal with the luminal connector 1203 about 0.12 inches from the end of the luminal connector 1203. The second barb fitting 1231 has a similar configuration and terminates at a surface substantially orthogonal with the luminal connector 1203 about 0.23 inches from the end of the luminal connector. These barb fittings 1221,1231 allow a flexible hose or tubing to be passed over the top of the luminal connector 1203, over the barb fittings 1221,1231, to the sloped luminal connector transition 1220. The surfaces substantially orthogonal with the luminal connector 1203 are then able to grasp the flexible tubing and retain it along the luminal connector 1203. Multiple barb fittings are more frequently used when the corresponding connector portion is less likely to be disconnected from the tubing to which it is coupled.

The unitary male connector portion 1200 includes a convex frustum 1201 extending from the cylindrical segmentum 1218 towards the protruding male connector portion 1202. The convex frustum 1201 is configured as a portion of a cone having convex sidewalls that has its upper part cut off by the cylindrical segmentum 1218. The convex sidewalls provide a softly tapering surface that has a quadruple-action function: First, the softly tapering surface provides an aesthetically pleasing design. Second, the softly tapering surface provides an easily graspable surface. Third, the softly tapering surface provides a surface suitable for logos, brand marks, text, or other indicia. Fourth, the softly tapering surface provides a smooth surface that will not irritate a patient lying atop the unitary male connector portion 1200.

Extending distally away from the convex frustum is the protruding male connector portion 1202. In one embodiment, the protruding male connector portion 1202 is about 0.515 inches. The protruding male connector portion 1202 has a width of about 0.510 inches.

As with the insertion region (601) of the unitary female connector portion (100), the protruding male connector portion 1202 can be fitted with mechanical features configured to retain the unitary male connector portion 1200 to a corresponding female connector portion. In this illustrative embodiment, a plurality of radial snap fitting recesses 1262, 1263. Each of the explanatory radial snap fitting recesses 1262,1263 has a depth of about 0.12 inches. As noted above, the radial snap fitting recesses 1262,1263 can be configured to mate with radial snap fitting protrusions on a complementary female connector portion. While radial snap fitting recesses 1262,1263 are used in the unitary male connector portion 1200, the complementary fitting element could be used instead. Said differently, the unitary male connector portion 1200 could include radial snap protrusions, while the female connector portion could include the radial fitting recesses. Alternatively, instead of recesses and protrusions, other mechanical coupling elements such as reversible barb fittings, ramp and latch fittings, friction fittings, and so forth could be used.

In one embodiment, the unitary male connector portion 1200 is manufactured by a single material by way of an injection molding process where the entire part is made within a single tool. For instance, the unitary male connector portion 1200 can be manufactured with a rigid thermoplastic material such as polypropylene. Polypropylene is a very suitable material due to its waxy surface. This waxy surface provides a lubricating effect such that the protruding male connector portion 1202 can easily be inserted into, and removed from, the insertion region of a corresponding female connector portion. The polypropylene or other thermoplastic, e.g., styrene, PVC, etc., can be colored in some embodiments. In one embodiment, the polypropylene or thermoplastic can be colored grey, with an explanatory example being PMS 430 grey.

Figure 21:
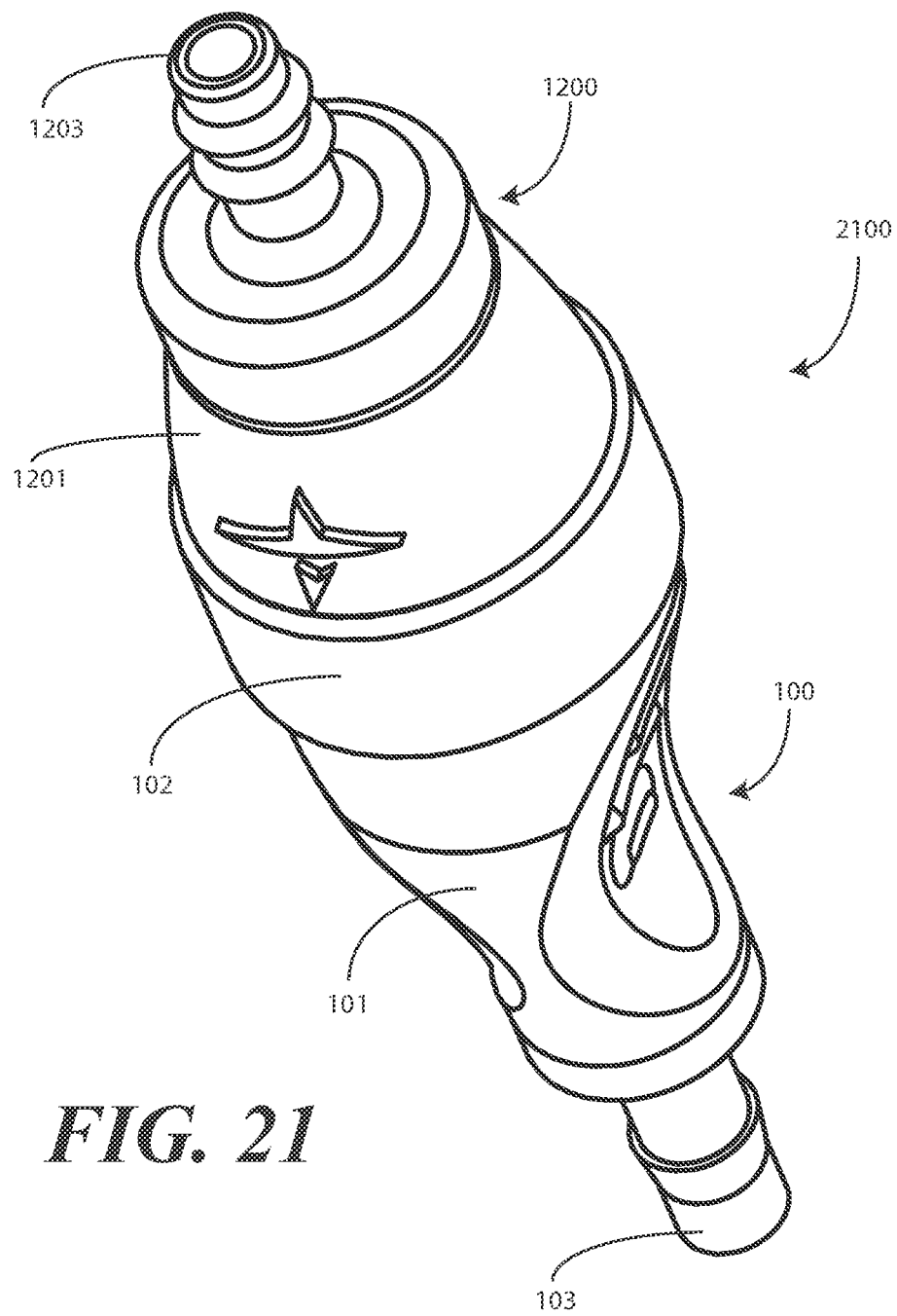
FIG. 21 illustrates a perspective view of a connector assembly having one unitary single ended female connector portion coupled to a single ended male connector portion in accordance with one or more embodiments of the invention.
Figure 22:
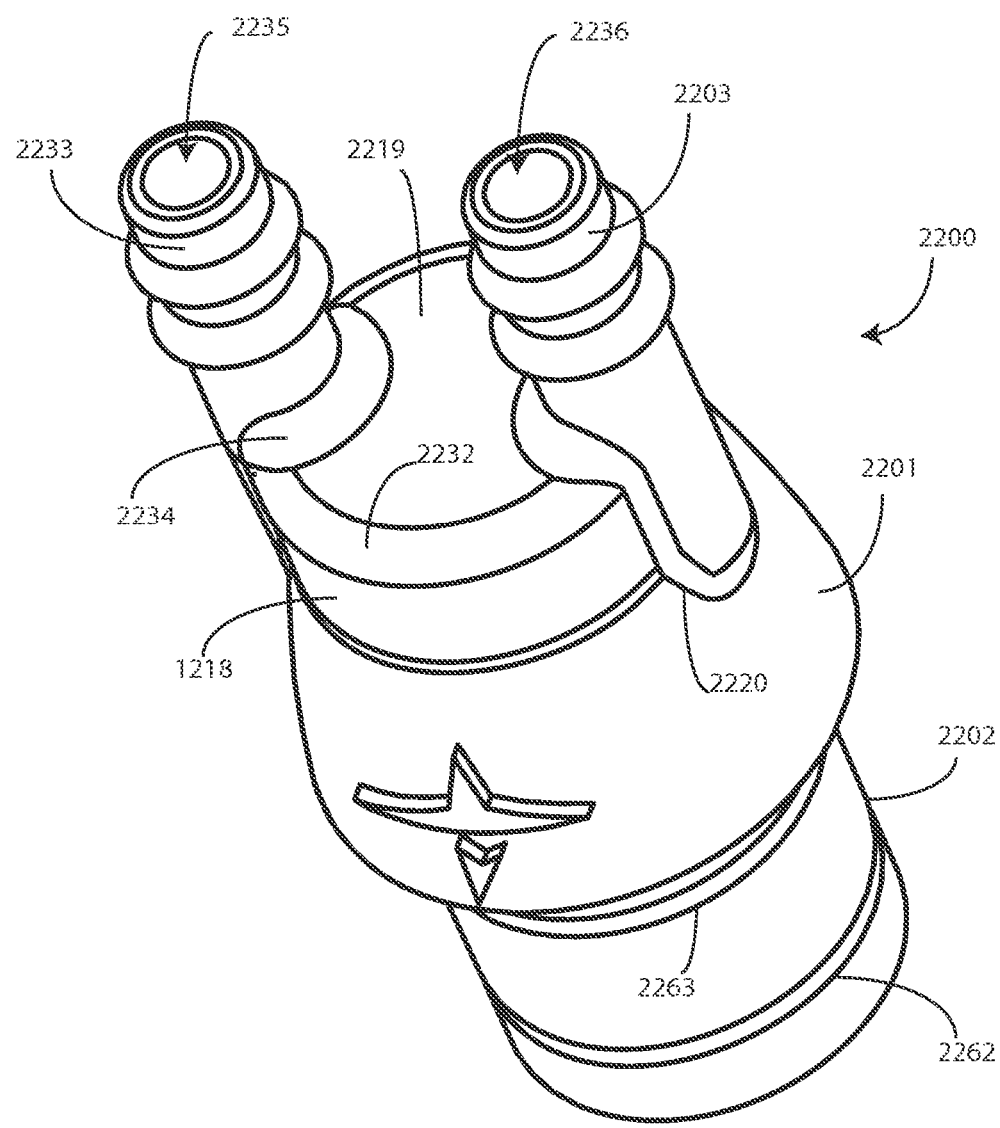
FIG. 22 illustrates a perspective view of one unitary double-ended male connector portion configured in accordance with one or more embodiments of the invention.
Figure 23:
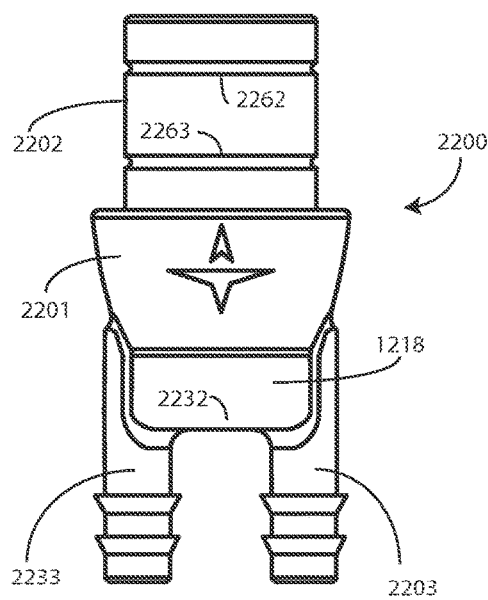
FIG. 23 illustrates a side elevation view of one unitary double-ended male connector portion configured in accordance with one or more embodiments of the invention.
Figure 24:
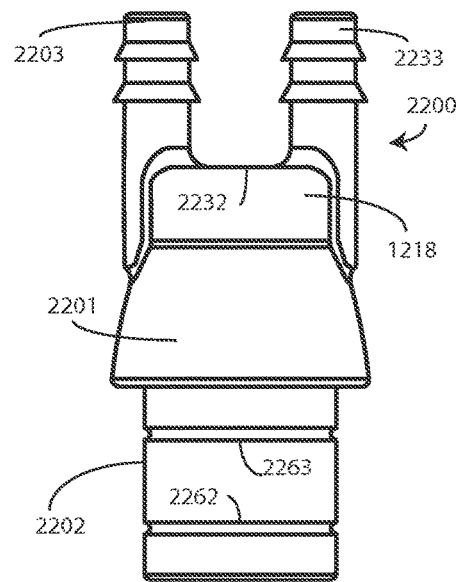
FIG. 24 illustrates a second side elevation view of one unitary double-ended male connector portion configured in accordance with one or more embodiments of the invention.
Figure 25:
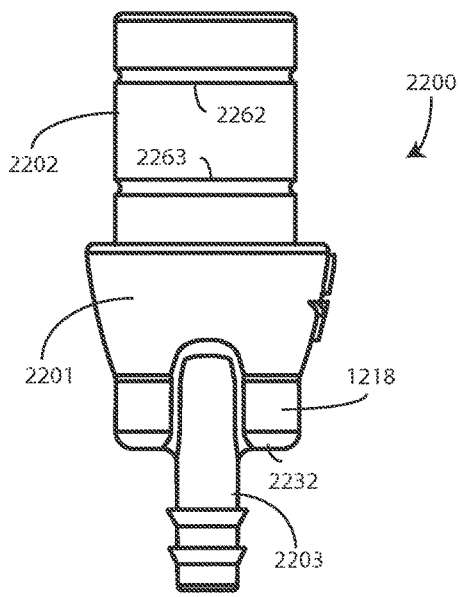
FIG. 25 illustrates a third side elevation view of one unitary double-ended male connector portion configured in accordance with one or more embodiments of the invention.
Figure 26:
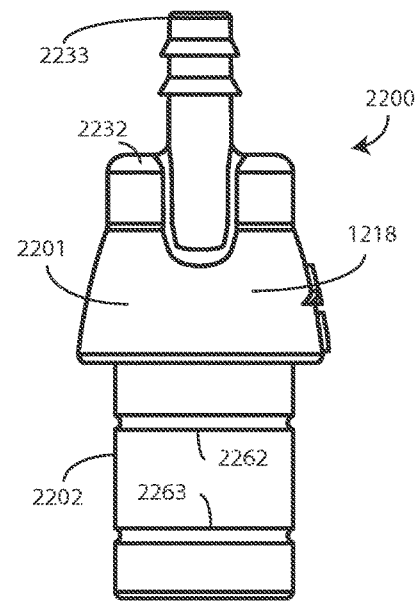
FIG. 26 illustrates a fourth side elevation view of one unitary double-ended male connector portion configured in accordance with one or more embodiments of the invention.

An assembled connector assembly 2100 is shown in FIG. 21. A unitary male connector portion 1200 has been coupled to a unitary female connector portion 100 by inserting the protruding male connector portion of the unitary male connector portion 1200 into the insertion region of the unitary female connector portion. The unitary male connector portion 1200 is selectively attachable to, and removable from, the unitary female connector portion 100. The assembly has an airtight seal between portions due to the elastomeric thermoplastic of the unitary female connector portion 100 wrapping about the rigid thermoplastic of the unitary male connector portion 1200. No O-rings are needed, as the radial snap fitting protrusions of the unitary female connector portion 100 seat within the radial snap fitting recesses of the unitary male connector portion 1200. In one embodiment, when the protrusions seat within the recesses, an audible click can be heard, thereby notifying the user that the airtight seal has been formed.

The assembly is easy to put together and take a part. In one embodiment the force required to separate the unitary male connector portion 1200 from the unitary female connector portion 100 can be adjusted by adjusting the height of the radial snap fitting protrusions and the corresponding depth of the radial snap fitting recesses. In one embodiment, the height and depth of the protrusions and recesses is selected such that an airtight seal is formed, yet that the components separate before corresponding equipment is toppled. Illustrating by example, when the assembly is used in a blood pressure application, a patient may flail or otherwise move when the blood pressure cuff is tethered—via the assembly—to an expensive blood pressure monitoring machine. Accordingly, the 0.012-inch height of the protrusions and corresponding depth of the recesses is selected such that the portions separate to prevent a patient from toppling a standard blood pressure monitoring machine.

Another advantage offered by embodiments of the present invention becomes visible in FIG. 21. Specifically, the smoothed, continuous surface provided by the compression ring 102, the waisted, tapering intermediate section 101, and the convex frustum 1201 provides a snag-free surface that is useful when the connector assembly 2100 is used in a medical application. Consider, for example, when the connector assembly 2100 is used in a blood pressure application. Frequently, a patient will be wearing a gown. Traditional, prior art connectors, such as Y-line connectors, have a tendency to snag in clothing. This snagging increases the risk that the flexible tubing or hoses can become disconnected from the connector. The contoured surface provided by the compression ring 102, the waisted, tapering intermediate section 101, and the convex frustum 1201 has no sharp corners, nooks, or crevices in which clothing can become snagged, thereby reducing the risk that flexible tubing or hoses will detach from the connector assembly 2101. The compression ring 102 forms a contoured band, while the waisted, tapering intermediate section 101 and the convex frustum 1200 gently taper away to the luminal connectors 103,1203.

Turning now to FIGS. 22-30, illustrated therein is a unitary double-ended male connector portion 2200 configured in accordance with one or more embodiments of the invention. The unitary double-ended male connector portion 2200 is a unitary connector portion in that it, like the other connector portions described above, is manufactured from a singular material. In one embodiment, this singular material is polypropylene. It will be clear to those of ordinary skill in the art that other materials could also be used.

Many elements of the unitary double-ended male connector portion 2200 are the same as on the single ended unitary male connector portion (1200) shown in FIGS. 12-20, including the convex frustration 2201, the protruding male connector portion 2202, and the radial snap fitting recesses 2262,2263. As these elements are the same as those used in the single ended male connector portion (1200) described above, they will not be discussed further here in the interest of brevity.

The unitary double-ended male connector portion 2200 differs from its single ended counterpart at the end disposed opposite the convex frustration 2201 from the protruding male connector portion 2202. Rather than having a single luminal connector, the unitary double-ended male connector portion 2200 includes a double-ended luminal connector comprising two luminal connectors 2203,2233 disposed 180 degrees apart along the semi-cylindrical segmentum 2218. Note that the semi-cylindrical segmentum 2218 is "semi-cylindrical" because the base portion of each luminal connector 2203,2233 interrupts this element at opposite sides and extends from the outer sides of the semi-cylindrical segmentum 2218.

The exterior of each of the luminal connectors 2203,2233 is substantially same as that described above with reference to the single ended male connector portion (1200). For instance, each of the luminal connectors 2203,2233 can include barb fittings. In this illustrative embodiment, two barb fittings are employed, with each being configured as a ramp disposed along its corresponding luminal connector 2203,2233. These barb fittings allow a flexible hose or tubing to be passed over the top of the luminal connectors 2203,2233, and over the barb fittings, to the sloped luminal connector transitions 2220,2234 tapering from the luminal connector base 2219.

A semi-annular transition surface 2232 is disposed between the semi-cylindrical segmentum 2218 and the luminal connector base 2219. The semi-annular transition surface 2232 of this illustrative embodiment is a convex surface having a circumference that narrows as the semi-annular transition surface 2232 extends away from the semi-cylindrical segmentum 2218. This provides a rounded contour that adds to the comfort of the overall connector portion when a patient inadvertently rolls over or otherwise finds himself or herself atop the unitary double-ended male connector portion 2200.

A second similarity between the unitary male connector portion 1200 and the unitary female connector portion (100) described above is the use of a luminal connector base 1219 configured as a disk-shaped plane. The luminal connector base 1219 extends from a rounded contour 1230 disposed between the cylindrical segmentum 1218 to the sloped luminal connector transition 1220. The sloped luminal connector transition 1220, which can be flat, convex, or concave, is configured in this embodiment as a convex surface running from the luminal connector base 1219 to the bottom of the luminal connector 1203.

Figure 27:
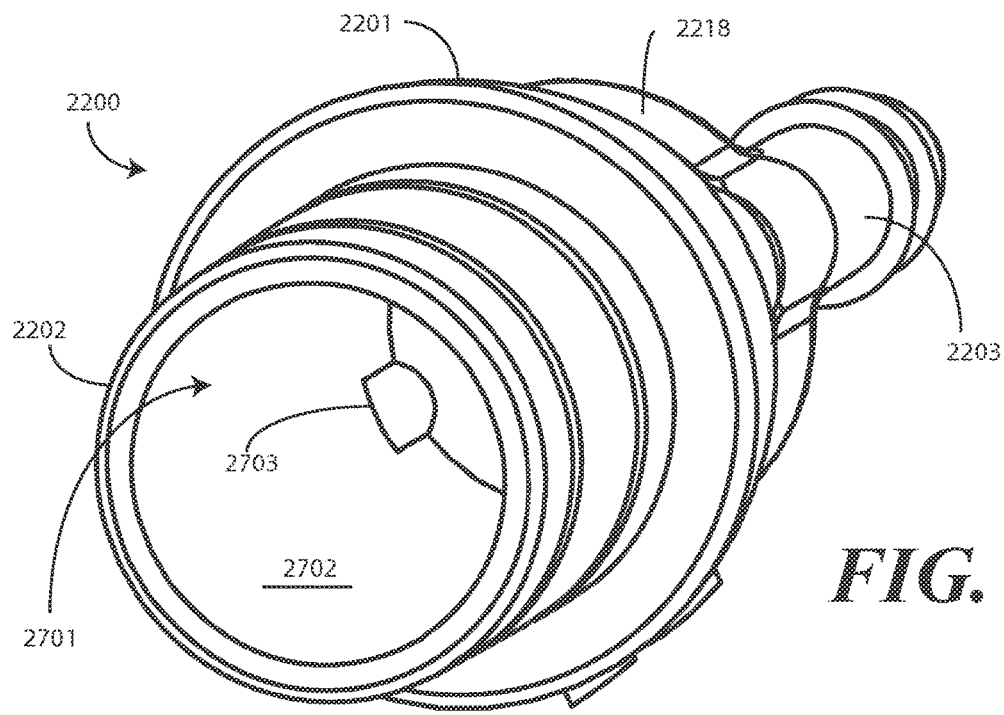
FIG. 27 illustrates a second perspective view of one unitary double-ended male connector portion configured in accordance with one or more embodiments of the invention.
Figure 28:
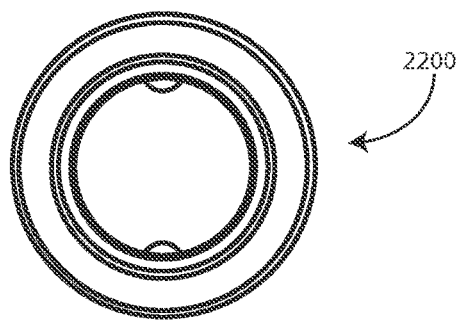
FIG. 28 illustrates a bottom plan view of one unitary double-ended male connector portion configured in accordance with one or more embodiments of the invention.
Figure 29:
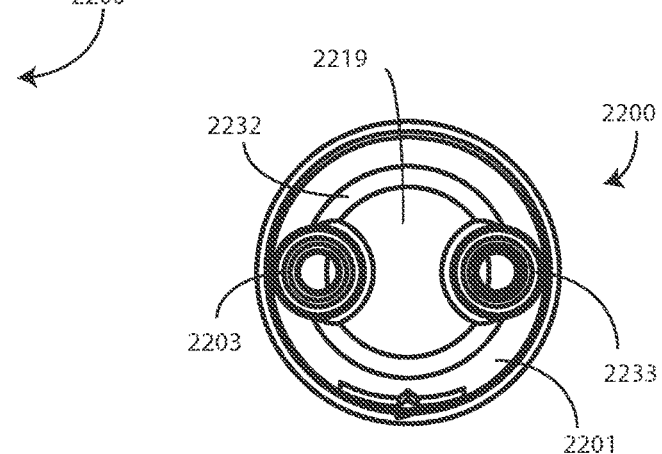
FIG. 29 illustrates a top plan view of one unitary double-ended male connector portion configured in accordance with one or more embodiments of the invention.

As shown best in FIG. 27, the protruding male connector portion 2202 and the convex frustration 2201 define an interior cavity 2701 just as the same components did for the single ended male connector portion (1200) as shown in FIGS. 17 and 18 above. This interior cavity 2701 is bounded laterally by sidewalls 2702. The interface between the interior cavity 2701 and the lumens (2235,2236) of each luminal connector (2203,2233) offers an advantageous and unique feature of embodiments of the present invention. The aperture 2703 defined between the interior cavity 2701 and the lumens (2235,2236) of each luminal connector (2203, 2233) is designed, in one embodiment, to have substantially the same cross-sectional area as each of the lumens (2235, 2236). In one embodiment, this cross-sectional relationship is specifically designed so that flow of air or liquid from the lumens (2235,2236) to the interior cavity 2701 is unimpeded.

Figure 30:
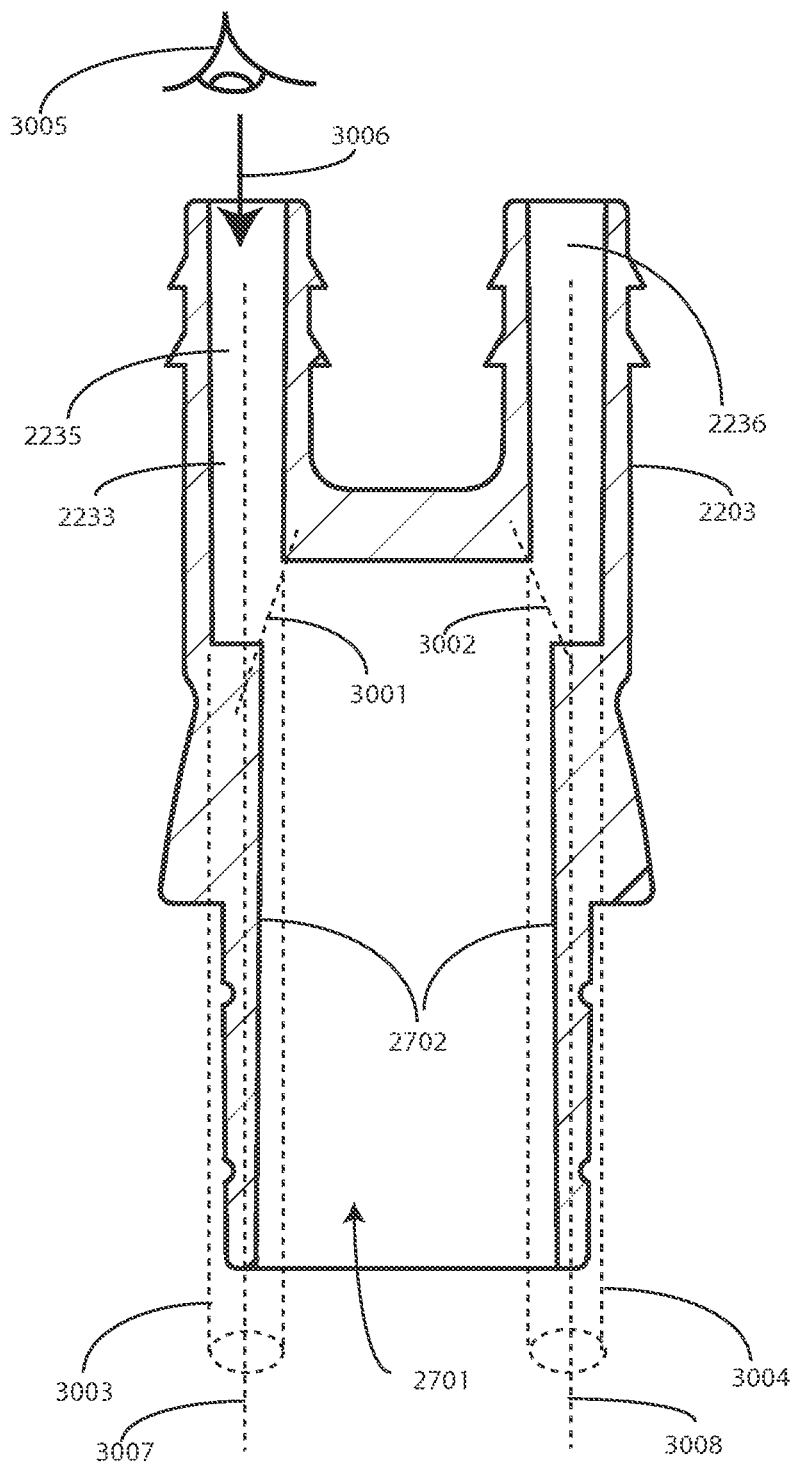
FIG. 30 illustrates a sectional view of one unitary double-ended male connector portion configured in accordance with one or more embodiments of the invention.

Turning to FIG. 30, this design criterion can more readily be seen. Luminal connector 2203 defines lumen 2236. Similarly, luminal connector 2233 defines lumen 2235. As noted above, the unitary double-ended male connector portion 2200 can be manufactured from a singular material, such as polypropylene, via an injection molding process. During this process, lumens 2235,2236 are formed by inserting core pins into the void defining each luminal connector 2203,2233 prior to injection of the singular material. Similarly, a larger core pin is inserted into the void defining the protruding male connector portion 2202 prior to injection of the singular material. The intersection of these core pins occurs at lines 3001,3002 of FIG. 30. In one embodiment of the invention, the cross-sectional area occurring at these lines 3001,3002 is specifically selected to be equal to the cross-sectional area of the core pins forming each lumen 2235,2235.

Another way to describe this is as follows: in one embodiment of the unitary double-ended male connector portion 2200, the luminal connectors 2203,2233 of the double-ended luminal connector are arranged in an offset configuration relative to the interior cavity 2701 such that the sidewalls 2702 pass through a cylinder 3003,3004 defined by each lumen 2235,2236 of each luminal connector 2203,2233. When this occurs, the sidewalls become visible to an observer 3005 looking 3006 into one or the other of the luminal connectors 2203,2233 along an axis 3007,30008 of the corresponding cylinder 3003,3004. In short, the luminal connectors 2203,2233 of the double-ended luminal connector are arranged in an offset configuration relative to the interior cavity 2701 such that the sidewalls 2702 pass through a cylinder 3003,3004 defined by each lumen 2235, 2236 of each luminal connector 2203,2233 such that the sidewalls 2702 are visible when looking into either luminal connector 2203,2233 along an axis 3007,3008 of a corresponding cylinder 3003,3004. Alternatively, a cross section defined at an intersection of each luminal connector 2203, 2233 and the interior cavity 2701, in one embodiment, is substantially equal to a luminal cross section of each lumen 2235,2236 of the each luminal connector 2203,2233.

Figure 31:
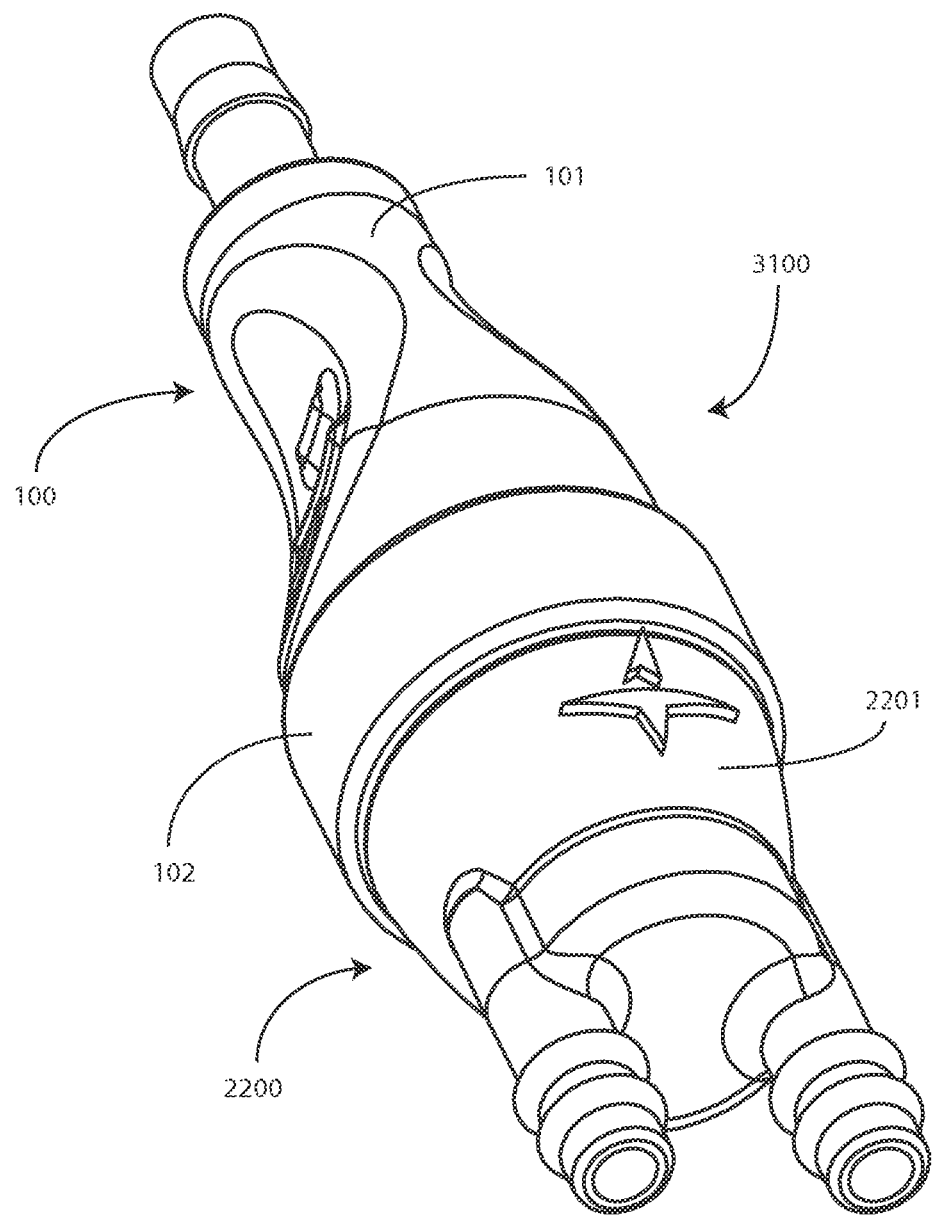
FIG. 31 illustrates a perspective view of one unitary double-ended male connector portion coupled to one unitary single ended female connector portion configured in accordance with one or more embodiments of the invention.
Figure 32:
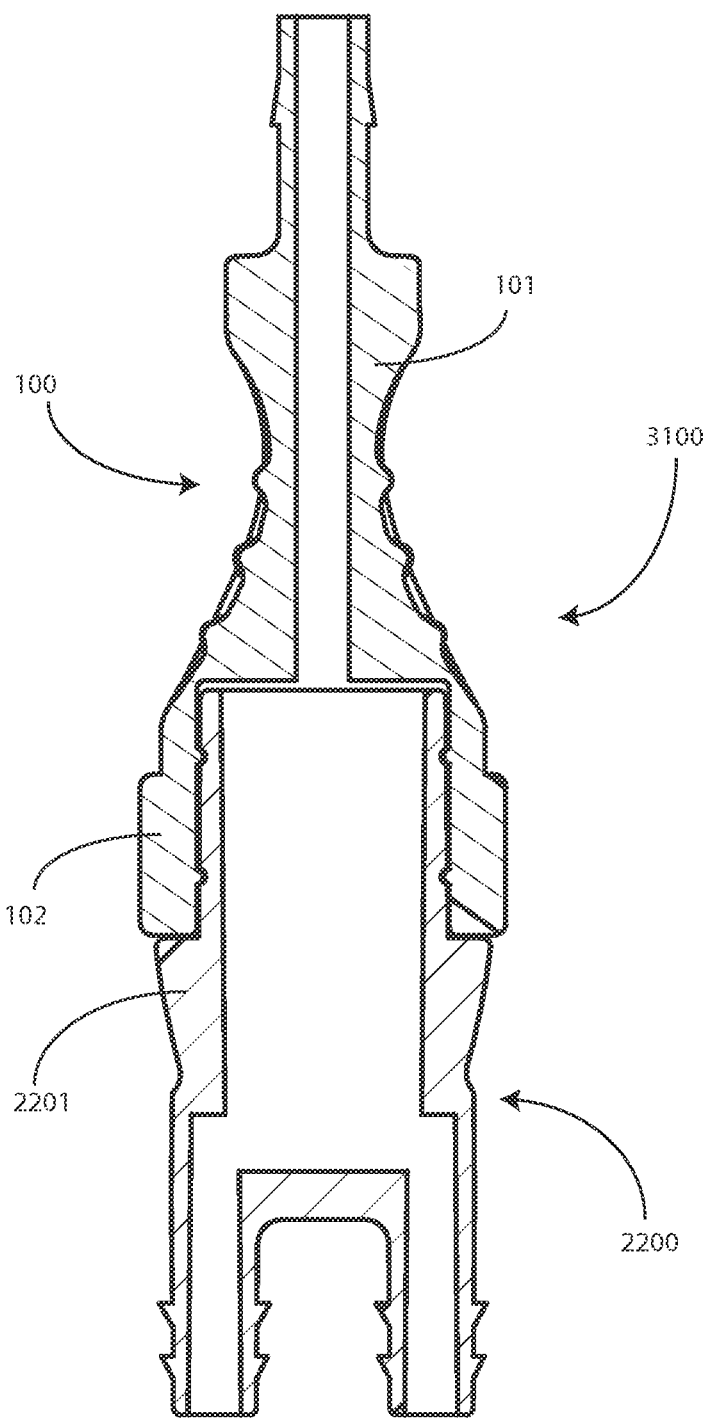
FIG. 32 illustrates a sectional view of one unitary double-ended male connector portion coupled to one unitary single ended female connector portion configured in accordance with one or more embodiments of the invention.

An assembled connector assembly 3100 is shown in FIGS. 31 and 32. FIG. 31 illustrates a perspective view of the assembly 3100, and FIG. 32 illustrates a sectional view of the assembly 3100. A unitary double-ended male connector portion 2200 has been coupled to a unitary female connector portion 100 by inserting the protruding male connector portion of the unitary double-ended male connector portion 2200 into the insertion region of the unitary female connector portion. The unitary double-ended male connector portion 2200 is selectively attachable to, and removable from, the unitary female connector portion 100. The assembly has an airtight seal between portions due to the elastomeric thermoplastic of the unitary female connector portion 100 wrapping about the rigid thermoplastic of the unitary double-ended male connector portion 2200. No O-rings are needed, as the radial snap fitting protrusions of the unitary female connector portion 100 seat within the radial snap fitting recesses of the unitary double-ended male connector portion 2200. In one embodiment, when the protrusions seat within the recesses, an audible click can be heard, thereby notifying the user that the airtight seal has been formed.

The assembly is easy to put together and take a part. Moreover, the streamlined, smoothly contoured outline of the assembly 3100 prevents irritation of a patient's skin when the patient is resting upon the assembly 3100.

The assembly 3100 offers the snag-free contoured surface described above with reference to FIG. 21. Specifically, the smoothed, continuous surface provided by the compression ring 102, the waisted, tapering intermediate section 101, and the convex frustum 2201 provides a snag-free surface that is useful when the connector assembly 3100 is used in a medical application. The contoured surface provided by the compression ring 102, the waisted, tapering intermediate section 101, and the convex frustum 2201 has no sharp corners, nooks, or crevices in which clothing can become snagged, thereby reducing the risk that flexible tubing or hoses will detach from the connector assembly 3100. The compression ring 102 forms a contoured band, while the waisted, tapering intermediate section 101 and the convex frustum 2201 gently taper away to the luminal connectors.

As shown and described, problems with prior art connectors have been solved with embodiments of the present invention. A female connector portion made of an elastomeric thermoplastic replaces rigid metal and plastic prior art designs. The male connector portion, which can be single ended or double-ended, when coupled to the female connector portion, allows embodiments of the present invention to be compatible directly with different types of blood pressure equipment. Moreover, connectors configured in accordance with embodiments of the invention can be used in any number of applications other than that of blood pressure monitoring. Both male and female connector portions can be manufactured by injection molding from a single material. Further, neither connector portion requires any secondary manufacturing operations such as machining or assembly of subcomponents. The connection and disconnection of the male and female connector portions is performed with a simple, straight, z-axis push or pull with moderate force. The male connector portion is smoothly contoured for comfort, while the female connector portion includes ergonomically designed finger depressions for better grip when disassembling.

In the foregoing specification, specific embodiments of the present invention have been described. However, one of ordinary skill in the art appreciates that various modifications and changes can be made without departing from the scope of the present invention as set forth in the claims below. Thus, while preferred embodiments of the invention have been illustrated and described, it is clear that the invention is not so limited. Numerous modifications, changes, variations, substitutions, and equivalents will occur to those skilled in the art without departing from the spirit and scope of the present invention as defined by the following claims. Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims.

What is claimed is:

1. A connector assembly comprising:
a unitary female connector portion manufactured from a singular material, the unitary female connector portion comprising:
a waisted, tapering intermediate section disposed between a compression ring and a luminal connector; and one or more finger grasping surfaces disposed along the waisted, tapering intermediate section;
wherein the one or more finger grasping surfaces each comprise a plurality of scalloped finger grips.

2. The connector assembly of claim 1, wherein the waisted, tapering intermediate section comprises two finger grasping surfaces disposed opposite each other along the waisted, tapering intermediate section so as to define a first waist diameter running across either finger grasping surface and a second waist diameter running between the two finger grasping surfaces, wherein the second waist diameter is less than the first waist diameter.

3. The connector assembly of claim 1, wherein each of the scalloped finger grips terminates at a planar segmentum spanning its corresponding scalloped finger grip.

4. The connector assembly of claim 1, wherein each of the one or more finger grasping surfaces comprises a convex semi-asymmetrically ovular grasping plane.

5. The connector assembly of claim 4, further comprising a transition surface disposed between the convex semi-asymmetrically ovular grasping plane and the waisted, tapering intermediate section, wherein the transition surface is non-planar with either of the convex semi-asymmetrically ovular grasping plane or the waisted, tapering intermediate section.

6. The connector assembly of claim 1, wherein the compression ring defines a receiving chamber comprising one or more radial snap protrusions.

7. The connector assembly of claim 1, wherein the singular material comprises an elastomeric thermoplastic.

8. The connector assembly of claim 1, wherein the connector assembly further comprises a single ended male connector portion selectively attachable to, and removable from, to the unitary female connector portion.

9. The connector assembly of claim 1, wherein the connector assembly further comprises a double-ended male connector portion selectively attachable to, and removable from, the unitary female connector portion.

10. A connector assembly comprising:
a single ended male connector portion manufactured from a singular material, the single ended male connector portion comprising:
a protruding male connector portion;
a single ended luminal connector; and
a convex frustration disposed between the protruding male connector portion and the single ended luminal connector.

11. The connector assembly of claim 10, further comprising a cylindrical frustum segmentum disposed between the convex frustration and the single ended luminal connector.

12. The connector assembly of claim 11, further comprising an annular transition surface having a circumference section that narrows as the annular transition surface extends away from the cylindrical frustum segmentum.

13. The connector assembly of claim 10, wherein the protruding male connector portion comprises one or more radial snap recesses disposed about a periphery of the protruding male connector portion.

14. The connector assembly of claim 10, further comprising a unitary female connector portion selectively attachable to, and removable from, the single ended male connector portion.

15. The connector assembly of claim 14, wherein the compression ring, the waisted, tapering intermediate section, and the convex frustum form a contoured, snag-resistant surface.

16. A connector assembly comprising double ended male connector
a double-ended male connector portion manufactured from a singular material, the double-ended male connector portion comprising:
a protruding male connector portion;
a double-ended luminal connector; and
a convex frustration disposed between the protruding male connector portion and the double-ended luminal connector.

17. The connector assembly of claim 16, wherein:
the convex frustration and the protruding male connector portion define an interior cavity having sidewalls; and
luminal connectors of the double-ended luminal connector are arranged in an offset configuration relative to the interior cavity such that the sidewalls pass through a cylinder defined by each lumen of each luminal connector such that the sidewalls are visible when looking into the each luminal connector along an axis of the cylinder.

18. The connector assembly of claim 16, wherein:
the convex frustration and the protruding male connector portion define an interior cavity having sidewalls; and
a cross section defined at an intersection of each luminal connector and the interior cavity is substantially equal to a luminal cross section of each lumen of the each luminal connector.

19. The connector assembly of claim 16, further comprising a unitary female connector portion selectively attachable to, and removable from, the double-ended male connector portion.

* * * * *